United States Patent [19]

Omura et al.

[11] Patent Number: 4,648,844

[45] Date of Patent: Mar. 10, 1987

[54] DENTAL LINING COMPOSITION

[75] Inventors: Ikuo Omura; Tatsuhiko Higaki; Junichi Yamauchi, all of Kurashiki, Japan

[73] Assignee: Kuraray Co., Ltd., Kurashiki, Japan

[21] Appl. No.: 837,965

[22] Filed: Mar. 10, 1986

[30] Foreign Application Priority Data

Mar. 22, 1985 [JP] Japan .................................. 60-59140

[51] Int. Cl.[4] .............................................. A61K 5/07
[52] U.S. Cl. ............................ 433/217.1; 433/199.1; 433/228.1; 523/115; 523/116; 523/118
[58] Field of Search ...................... 523/115, 116, 118; 433/199.1, 217.1, 228.1

[56] References Cited

U.S. PATENT DOCUMENTS 4,302,381 11/1981 Omura et al. ...................... 523/118
4,396,378 8/1983 Orlowski et al. ................... 523/118

Primary Examiner—Lorenzo B. Hayes
Attorney, Agent, or Firm—Oblon, Fisher, Spivak, McClelland & Maier

[57] ABSTRACT

This invention relates to two-pack type dental lining compositions comprising (a) a solution of a polymer having at least 10 mole % of a carboxyl-containing vinyl monomer, and (b) a solution of a zirconium chelate compound represented by the following general formula

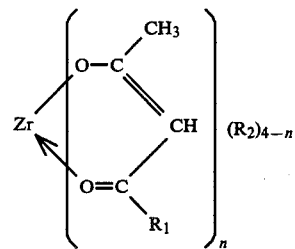

(wherein $R_1$ denotes $-CH_3$, $-OCH_3$ or $-OCH_2CH_3$, $R_2$ stands for an alkoxy of 2 to 10 carbon atoms, and n is an integer from 2 to 4).

5 Claims, No Drawings

DENTAL LINING COMPOSITION

FIELD OF THE INVENTION

This invention relates to dental lining compositions to be applied to the dentin surface in the tooth restorative treatment in order to prevent pulpal irritancy.

DESCRIPTION OF THE PRIOR ART

In the treatment of dental caries, it is a common practice to remove the affected part to the intact dentin with a bur and to plug the cavity thus formed with a resinous restorative material (such as composite resins), but in some of these treatments, patients complain of a toothache. It is generally accepted that the toothache is caused by the low-molecular compounds dissolved out from the composite resin, such as unpolymerized monomers and polymerization initiator, which reach the pulp through the dentinal tubules, thus inducing pulpitis and other troubles, or by poor adaptation of the applied restorative material to the cavity wall, which allows physical irritation (e.g., changes in hydrostatic pressure and temperature) to pass through the interstices and permits invasion of bacteria to induce inflammation. Covering of the dentin surface with a polymeric lining material is known as a means to prevent such pulpal irritancy (toothache, inflammation, necrosis, abscess and others), and polycarboxylate cement (powder component: ZnO, MgO; liquid component: polyacrylic acid) and glass ionomer cement (powder component: aluminosilicate glass; liquid component: polyacrylic acid) have long been used for this purpose (Journal of the Adhesion Society of Japan, Vol. 14, No. 12, 14–19, 1978). Cement of these types is applied in the form of a viscous paste prepared by mixing the two components immediately before use. Hence, the disadvantages are that, the succeeding restoration with a composite resin is difficult when the paste is applied to a shallow cavity (for example, a wedge-shaped defect on the cervical part) because the film of past formed is very thick, and that the cement, though suited for application to cavity floors, is rather unsuitable for application to cavity walls. In addition, these cement cannot be used for dentin protection in some instances where the clearance between prosthetic appliance and the tooth is very small, for example, for abutment teeth with exposed dentin before cast crowns are set. Furthermore, the cement of these types has poor adhesion to the dentin and is not highly durable in the mouth because it tends to come into solution by the action of saliva.

New types of lining compositions have recently been disclosed as a substitute for the conventional pasty cement, which comprise two liquid components to be mixed immeidately before use and are capable of forming a thin coating film. Japanese Patent Application Laid-open No. 219,277 (1983) teaches lining compositions composed mainly of a copolymer of maleic acid and a radically copolymerizable vinyl compound having a hydrophobic group (for example, styrene/maleic acid copolymers) and a polyvalent metal salt (for example,. $CaCl_2$, $FeCl_3$ and $AlCl_3$). Japanese Patent Application Laid-open No. 30,877 (1984) (corresponding European Patent Publication No. 103,420) discloses lining compositions comprising a copolymer as defined above and an organic titanate, such as tetraisopropyl titanate, tetra-n-butyl titanate, diisopropoxy bis(acetylacetone)titanate and tetrakis(2-ethylhexyl)titanate. The former compositions empolying a polyvalent metal salt are unsatisfactory in resistance to water and in the ability to block irritant substances, such as monomers, while the latter compositions using an organic titanate are insufficient in adhesion to the dentin and in the ability to block irritant substances. Many organic titanates also have the problem of being unstable against commonly used solvents, such as water and ethanol.

SUMMARY OF THE INVENTION

The object of this invention is to provide new dental lining compositions which are better than conventional lining compositions in the following points:

1. Can be handled and applied more easily, and can be thinly coated on the dentin surface.
2. High adhesion to the tooth and high sealability, which effectively blocks pulpal irritancy factors (unpolymerized monomers dissolved out from composite resin, bacteria, and others) to ensure complete protection of the dental pulp.
3. Higher storage stability.

These objects can be achieved by two-component, dental lining compositions comprising (a) a solution of a polymer having at least 10 mole % of a carboxyl-containing vinyl monomer, and (b) a solution of a zirconium chelate compound represented by the following general formula

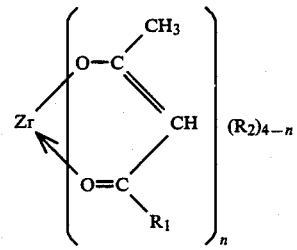

(wherein $R_1$ denotes $-CH_3$, $-OCH_3$ or $-OCH_2CH_3$, $R_2$ stands for an alkoxy of 2 to 10 carbon atoms, and n is an integer from 2 to 4).

DETAILED DESCRIPTION OF THE INVENTION

The polymer used as a component of the dental lining composition of this invention must have at least 10 mole % of carboxyl-containing vinyl monomer units to ensure sufficient adhesion to the tooth. Such polymers may be a homopolymer of a carboxyl-containing vinyl monomer, or a copolymer having a carboxyl-containing vinyl monomer as a constituent. As examples of the homopolymers may be mentioned poly(acrylic acid), poly(methacrylic acid), poly(maleic acid), poly(fummaric acid) and poly(p-vinylbenzoic acid). Typical examples of the carboxyl-containing copolymers include acrylic acid/methacrylic acid copolymers, acrylic acid/maleic acid copolymers, acrylic acid/itaconic acid copolymers, methacrylic acid/acrylonitrile copolymers, styrene/maleic acid copolymers, isobutene/maleic acid copolymers, ethylene/maleic acid copolymers, methyl vinyl ether/maleic acid copolymers, ethylene/acrylic acid copolymers, ethylene/methacrylic acid copolymers, vinyl alcohol/crotonic acid copolymers, isobutene/butyl maleate copolymers, styrene/ethyl maleate copolymers, and styrene/maleinamide copolymers. The weight average molecular weight of these polymers should be at least 2000, more preferably at least 5000. If the molecular weight is less than 2000, film-forming properties will be poor. If the molecular weight exceeds 500000, on the other hand, the solution viscosity will be too high when the polymer is dissolved in solvents mentioned below, making handling of the solutions difficult. Furthermore, in order to obtain coatings with high resistance to water, it is preferable to use relatively hydrophobic polymers (among those whose molecualr weight is in the range specified above) in which the quotient of the total number of carbon atoms in the polymer divided by the number of carboxyl groups contained (hereinafter abbreviated as "$C/CO_2H$") is 4 or larger. Typical examples of such polymers include poly(methacrylic acid) ($C/CO_2H=4$), poly(p-vinylbenzoic acid) ($C/CO_2H=9$), 1:1 (mole ratio) styrene/maleic acid copolymer ($C/CO_2H=6$), 1:1 (mole ratio) isobutene/maleic acid copolymer ($C/CO_2H=4$), 1:1 (mole ratio) isobutene/butyl maleate copolymer ($C/CO_2H=6$), 2:1 (mole ratio) ethylene/maleic acid copolymer ($C/CO_2H=4$), 2:1 (mole ratio) ethylene/acrylic acid copolymer ($C/CO_2H=7$), 5:1 (mole ratio) ethylene/maleic acid copolymer ($C/CO_2H=7$), and 5:1 (mole ratio) ethylene/acrylic acid copolymer ($C/CO_2H=13$). Of these, stylene-maleic acid copolymer is most preferred.

In addition, modified styrene-maleic acid copolymers in which part of the maleic acid units are modified by aminosalicylic acid may also be used advantageously. These can be prepared by reaction of a styrene/maleic acid copolymer with aminosalicylic acid, and contain the following structural unit

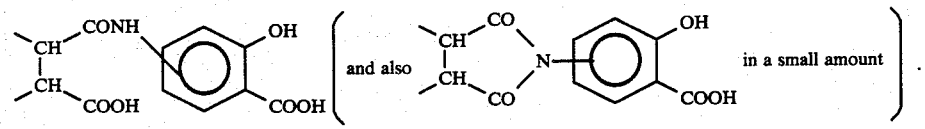

By so introducing a structural unit containing the radical

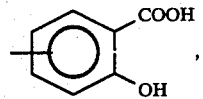

the polymer acquires higher affinity to both the Ca ions of the tooth and the zirconium chelate compound, thus giving dental lining compositions with further enhanced adhesion and water resistance. The amount of the radical

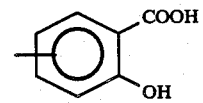

introduced should preferably be in the range of 0.10 to 0.60 molar fraction based on the maleic acid units. If its molar fraction exceeds 0.60, gelation upon addition of the zirconium compound proceeds too rapidly, making handling of the resulting dental lining composition very difficult.

The zirconium chelate compound used in this invention is a compound represented by the following general formula

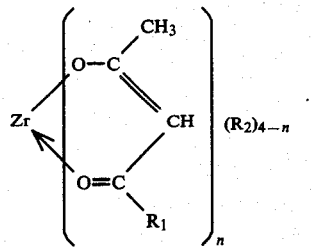

(wherein $R_1$ denotes —$CH_3$, —$OCH_3$ or —$OCH_2CH_3$, $R_2$ stands for an alkoxy of 2 to 10 carbon atoms, and n is an integer from 2 to 4). As examples of the alkoxy group in the above formula may be mentioned ethoxy, isopropoxy, n-propoxy, n-butoxy, benzyloxy and n-decanoxy. Illustrative examples of such zirconium chelate compounds are:

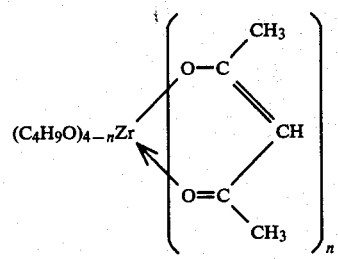

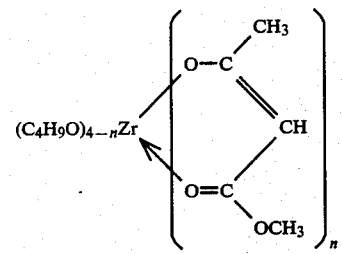

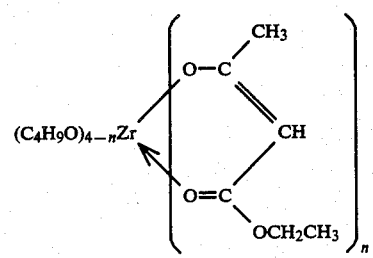

-continued

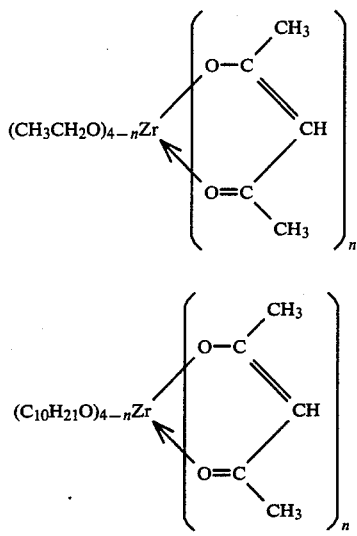

(wherein n is 2, 3 or 4).

The compounds given above are all stable against moisture. Of these, however, dibutoxy bis-(acetylacetonato)zirconium and tetrakis-(acetylacetonato)zirconium are the most preferred. Such zirconium compounds give stable solutions when disssolved in the solvents specified below, and are capable of effectively crosslinking the above-mentioned polymers, thus affording dental lining compositons with high adhesion and water resistance.

Compounds or titanium, aluminum, tin, iron and calcium could also be used as a crosslinker for the above-mentioned polymers, but the compounds of zirconium are the best in terms of the stability of crosslinks formed.

What is important to note is that not all zirconium compounds serve the purpose. For example, zirconocene dichloride is a toxic compound and cannot be used in medical materials. Tetraethyl zirconate, tetra-n-butyl zirconate and similars are subject to rapid hydrolysis upon contact with trace moisture, and hence their storage stability in the form of solutions is very low. In addition, these fail to give lining compositions with satisfactory adhesion to the tooth.

The polymers and zirconium compounds of this invention are used preferably as solutions in water or a nontoxic organic solvent boiling at 150° C. or lower under normal pressure. As typical examples of such solvents may be mentioned, among others, ethanol, isopropanol, n-propanol, n-butanol, acetone, methyl ethyl ketone, acetylacetone, isopropyl ether, n-butyl ether, ethyl acetate, n-amyl acetate, dichloromethane, 1,1,1-trichloroethane and toluene. These solvents may be used either alone or in combination. Water-miscible solvents, such as ethanol and acetone, may also be employed as a mixed solvent with water. Suitable solvents can be selected from those just mentioned so that the polymer and zirconium compound to be used will be dissolved to proper concentrations. It is also permissible to use different types of solvents (or mixed solvents of different compositions) to dissolve the polymer and the zirconium compound.

The concentration of polymer in solution should preferably be in the range of 0.1 to 60 weight %, most preferably in the range of 1 to 40 weight %. A concentration lower than 0.1 weight % gives too thin a coating film, which fails to show expected blocking effect. Solutions of more than 60 weight % concentration, on the other hand, are too viscous for easy coating operation. The concentration of zirconium chelate compund in solution should preferably be in the range of 0.01 to 60 weight %, most preferably in the range of 0.1 to 40 weight %. Concentrations below 0.01 weight % are not practical because of the slow setting of coating film and low mechanical strength of setted film. Solutions of more than 60 weight %, on the other hand, give too fast setting time for easy coating operation. It is preffered that the concentrations and mixing ratio of the polymer solution and the zirconium compound solution be selected so that the polymer/zirconium compound weight ratio will be at least 2. If this ratio is less than 2, it is hardly possible to obtain coating film that achieves the object of this invention, because the the amount of crosslinker is in excess compared with the polymer.

The solutin of polymer and the solution of zirconium chelate compound, which are separately packed and delivered in two-pack form, are mixed together immediately before use. The mixing ratio should preferably be in the range from 1:10 to 10:1 on weight basis, most preferably in the range from 3:1 to 1:3, for ease of handling. As crosslinking of polymer chains sets in upon mixing of the two components, it is preferable to apply the resulting solution to the tooth surface immediately after mixing and to dry the coating film as fast as possible by air spraing if necessary. Coating film firmly attached to the tooth will thus be obtained.

In order to modify the properties of coating film, the lining composition of this invention may contain, other than the essential components described above, various types of other polymers (e.g., PMMA, polystyrene, PVA, and ethylenevinyl alcohol copolymer), fine-particle filler, pigment and drugs such as analgesics and anti-inflammatory agents.

As described above, the dental lining composition of this invention contains, as main components, a polymer comprising a carboxyl-containing vinyl monomer and a zirconium chelate compound. The carboxyl groups in said polymer are capable of uniting with the calcium ions of the tooth, thus imparting the lining composition with good adhesion to the tooth, while the zirconium chelate compound, with its zirconium atom having high affinity to oxygen atom, tends to combine with the OH and COOH groups on the polymer chain to effect crosslinking. Lining film having high mechanical strength and high durability can thus be obtained.

With these characteristic features, the dental lining composition of this invention is expected to protect the dentin from acid etching, which is a pretreatment for tooth restoration with a composite resin. It is also effective in arresting the penetration of unpolymerized monomers and additives (e.g., polymerization initiator), dissolved out from the composite resins filled in cavities, into the dentin and in obstructing exteranl stimulation factors (changes in hydrostatic pressure and temperature, invasion of bacteria, etc.) caused by marginal leakage. Thus the lining composition of this invention will be able to prevent pulpal irritancy that might otherwise be caused by tooth restoration with composite resin.

The dental lining composition of this invention, which is of the liquid, two-pack type unlike conventional cement base (viscous paste), is easy to handle and can be rapidly and uniformly coated on the internal surface of cavities (cavity walls and floors), or over the entire surface area of abutment teeth, by means of a brush, a cotton or a sponge pellet. Dense lining film firmly attached to the tooth is left after the volatile solvent is evaporated by natural drying or by air spraying. The thickness of film thus obtained is normally as thin as 5 to 50 μm. Hence, the lining composition of this invention is applicable not only to the dentin of cavities, but also to the dentin of any other parts of possible pulpal irritancy, for example, abutment teeth with exposed dentin before cast crowns are set, and cervical dish-shaped cavities.

The ability of the lining composition of this invention to effectively prevent the penetration of irritant substances into the dentin and pulp will be apparent from the result described in Example 2 below. In fact, the lining composition of this invention can be clinically applied for composite resin plugging to cervical wedge-shaped defects of hypersensitive patients, and to many other cases where marked pulpal irritancy might otherwise be encountered.

The solution of the zirconium chelate compound used in this invention is stable against moisture and alcohols, with little deterioration (e.g., precipitation of insoluble matters) during storage as observed in the organic titanates described in Japanese Patent Application Laid-open No. 219,277 (1983). The lining composition of this invention is nontoxic to living bodies, with no hazardous effect upon the dental pulp.

The following examples will further illustrate this invention but are not intended to limit its scope.

EXAMPLE 1

A styrene/maleic anhydride copolymer (molar ratio; 1:1) having a weight average molecular weight of 31,000 was subjected to acid hydrolysis, giving a styrene/maleic acid copolymer. Lining compositions were prepared by combining this copolymer with each of the zirconium chelate compounds listed in Table 1. The copolymer was dissolved in ethanol or in an aqueous ethanol (water/ethanol ratio: 20/80 by volume) to a concentration of 9.0 weight %, while the zirconium compound was dissolved in water or in an aqueous ethanol of the same composition as above to a concentration of 1.7 weight % (the same solvent was used for the copolymer and zirconium compound in each case).

Adhesiveness of each of the two-pack lining compositions thus prepared was tested as follows. The labial surface of freshly extracted bovine foretooth was ground to expose the dentin, and the exposed surface was subjected to wet polishing with silicon carbide paper (1000 grit). After thorough washing with water, the polished surface was dried by nitrogen gas spraying, and a sheet of adhesive tape with a perforation of 5 mmφ was applied to the dry surface. Equal amounts of the two types of liquid components were taken on a mixing well and intimately mixed with a sponge pellet, and the mixture was coated on the tooth surface (at the perforation of the adhesive tape applied). Nitrogen gas was sprayed at once to evaporate the solvent, the same mixture as above was coated again, and the coated layer was left to natural drying. On the lining film thus formed was applied mixed paste of dental composite resin "Clearfil FII" (Kuraray, Co., Ltd.), and a fixture for tensile test was set in the resin. The specimen for adhesion test thus obtained was allowed to stand at room temperature for 30 minutes, immersed in 37° C. water for 24 hours, and tested on an Instron universal testing machine at a crosshead speed of 2 mm/min. Ten specimens were used for each test, and the average values are listed in Table 1.

TABLE 1

| No. | Zirconium Chelate Compound | Solvent | Bond Strength |
|---|---|---|---|
| 1-1 | Tetrakis(acetylacetonato)-zirconium | EtOH | 4.6 Kg |
| 1-2 | Dibutoxy bis(acetylacetonato)-zirconium | EtOH | 3.4 |
| 1-3 | Tetrakis(acetylacetonato)-zirconium | Water/EtOH (20/80) | 1.4 |
| 1-4 | Dibutoxy bis(acetylacetonato)-zirconium | Water/EtOH (20/80) | 1.4 |

EXAMPLE 2

For complete protectin of the pulp, a dental lining composition must have ability to block unpolymerized monomers, dissolved out from composite resin filled in cavities, thus preventing their entry to the dentin. The following simulation test using a dye in place of monomer was conducted to examine this capacity of lining composition.

A columnar cavity, 3 mm in diametr and 2 mm in depth, was formed in the labial surface of freshly extracted bovine tooth (foretooth) with a diamond bur. After being dried with nitrogen gas, the internal surface of the cavity was coated twice with the lining compound prepared in Example 1 in the same manner as above, followed by drying of the lining film formed. Phosphoric acid (35 weight %) was then applied by means of a sponge pellet, the cavity was thoroughly washed with water after about one minute and dried once again. Next, the catalyst solution for "Clearfil New Bond" (Kuraray Co., Ltd.) diluted with equal volume of ethanol was coated by using a sponge pellet, followed by washing with water after about one minute and drying. A 0.5% aqueous solution of basic fuchsin was poured into the cavity, its opening was sealed with a sheet of cover glass and dental wax, and the bovine tooth was held in an atmosphere of 37° C. and 100% humidity for 24 hours. It was then cut into three sections with a cutter to check how far the fuchsin had penetrated into the dentin. Test samples in which no penetration of fuchsin solution was observed were rated at "0", those in which penetration ended within the dentin were evaluated at "1", and those in which fuchsin solution reached the pulp cavity were evaluated at "2". Four pieces of teeth were tested for each lining composition and degree of penetration was determined by averaging the rating values of 12 sections. The result is summarized in Table 2.

TABLE 2

| No. | Zirconium Chelate Compound | Solvent | Penetration |
|---|---|---|---|
| 2-1 | Tetrakis(acetylacetonato)-zirconium | EtOH | 0.3 |
| 2-2 | Dibutoxy bis(acetylacetonato)-zirconium | EtOH | 0.5 |
| 2-3 | Tetrakis(acetylacetonato)-zirconium | Water/EtOH (20/80) | 0.7 |
| 2-4 | Dibutoxy bis(acetylacetonato)-zirconium | Water/EtOH (20/80) | 0.9 |

EXAMPLE 3

The following experiment was conducted to evaluate the marginal leakage at cavities coated with a lining composition and then plugged with a composite resin. Each of the lining compositions prepared in Example 1 was coated on the internal surface of a cavity in a bovine tooth formed in the same manner as in Example 2, followed by application of a dental adhesive "Clearfil New Bond" (Kuraray Co., Ltd.) according to the prescribed method and by plugging with a dental composite resin "Clearfil FII" (Kuraray Co., Ltd.). The whole piece of tooth except the cavity was covered with a dental self-curing resin, and the specimen thus prepared was immersed in 37° C. water for 24 hours. It was then polished with silicon carbide paper (1000 grit) to expose the marginal area of the cavity, and subjected to a heat cycle test; the sample was immersed alternately in 0.5% aqueous fuchsin solution held at 4° C. and in 0.5% aqueous fuchsin solution held at 60° C. for one minute each and this operation was repeated 100 times. The tested speicmen was then cut into five sections to check the penetration of fuchsin through the margin into the cavity wall. Test samples in which no penetration of fuchsin was observed were rated at "0", those in which penetration ended within the enamel were evaluated at "1", and those in which fuchsin solution reached the dentin at cavity floor were evaluated at "2". Four pieces of teeth were tested for each lining composition, and marginal leakage was determined by averaging the rating values of 20 sections. The test result is summarized in Table 3.

TABLE 3

| No. | Zirconium Chelate Compound | Solvent | Marginal Leakage |
|---|---|---|---|
| 3-1 | Tetrakis(acetylacetonato)-zirconium | EtOH | 0.1 |
| 3-2 | Dibutoxy bis(acetylacetonato)-zirconium | EtOH | 0.1 |
| 3-3 | Tetrakis(acetylacetonato)-zirconium | Water/EtOH (20/80) | 0.7 |
| 3-4 | Dibutoxy bis(acetylacetonato)-zirconium | Water/EtOH (20/80) | 0.4 |

EXAMPLE 4

In order to examine the stability of the zirconium chelate compounds of this invention against moisture, tetrakis(acetylacetonato)zirconium and bis-(acetylacetonato)zirconium dibutoxide were each dissolved in 95% ethanol (containing 5 volume % of water) to a concentration of 2%, and the solutions thus obtained were stored in a closed vessel at 50° C. for three months. No insoluble matters caused by hydrolysis were observed.

EXAMPLE 5

The sections used in Example 3 to examine marginal leakage were observed under an optical microscope at a magnification of 500X. The presence of a thin film of lining composition between the cavity wall and the composite resin was confirmed. The thickness of this film was in the range from 10 $\mu$m to 40 $\mu$m, indicating uniform spreading of the film over the entire cavity surface.

COMPARATIVE EXAMPLE 1

Specimens were prepared using fereshly extracted bovine teeth (foreteeth) in the same manner as Examples 1-4, except that known lining compositions, obtained by mixing an ethanolic solution of styrene/maleic acid copolymer with an ethanolic solution of an organic titanate, a zirconium alkoxy compound or a metal chloride, were used. Bonding strength, degree of dye penetration and marginal leakage of these specimens, as well as storage stability of these lining compositions, were measured, the result of which is summarized in Table 4. The styrene/maleic acid copolymer used in experiment No. 7 was prepared by hydrolysis of "SMA3000-"—Arco Chemical's styrene/maleic anhydride copolymer (molar ratio; 3:1, molecular weight; 1900)—in the same manner as in Example 1, and empoloyed as 9% ethanolic solution. The styrene/maleic acid copolymers used in the other experiments are the same one as in Example 1 and were also employed as 9% ethanolic solution.

TABLE 4

| No. | Types of Organic Titanates and Metal Chlorides, and Their Concentration in Ethanol (wt-%) | | Bonding Strength (Kg/cm$^2$) | Degree of Penetration | Marginal Leakage | Storage Stability |
|---|---|---|---|---|---|---|
| 1 | Dipropoxy bis(acetylacetonato)titanium | 1.7 | 0.7 | 1.5 | 0.4 | Turbid after 30 minutes |
| 2 | Dibutoxy bis(triethanolaminato)titanium | 1.7 | 0.1 | 1.3 | 0.5 | Good |
| 3 | Diydroxy bis(lactato)titanium | 1.7 | 0.2 | 1.6 | 0.4 | Good |
| 4 | Tetrapropoxy titanium | 1.7 | — | — | — | Decomposes upon dissolution |
| 5 | Tetrabutoxy titanium | 1.7 | — | — | — | Same as above |
| 6 | Tetra-iso-butoxy titanium | 1.7 | 0.4 | 1.9 | 1.8 | Turbid after 5 days |
| 7 | Ferric chloride | 0.7 | 1.1 | 2.0 | 0.3 | Precipitation after 10 days |
| 8 | Aluminum chloride | 4.5 | 0.8 | 1.9 | 0.2 | Good |

COMPARATIVE EXAMPLE 2

A cavity was formed in freshly extracted bovine tooth (foretooth) in the same manner as Example 5, and coated with commercial cement: zinc oxide-eugenol cement, polycarboxylate cement and glass ionomer cement. Each of the three samples thus prepared was treated in the same way as Example 5 to measure the thickness of lining film. The thickness was larger than 0.1 mm for all. It was demonstrated that uniform coating could not be achieved on cavity walls, the unevenness of thickness being very marked.

EXAMPLE 6

Manufacture of Modified Polymer

Fifteen grams of a styrene/maleic anhydride copolymer (molar ratio; 1:1, weight average molecular weight; 50000) was dissolved at room temperature in 135 g of dimethyl sulfoxide in a 0.5-liter reactor in a nitrogen atmosphere, and the solution was then heated to 120° C. To this was added dropwise a solution of 10 g p-aminosalicylic acid and 17 g triethylamine in 90 g dimethyl sulfoxide with stirring, and the reaction was continued at 120° C. for three hours. The reaction mixture was cooled to room temperature, 6N-HCl was added until the pH fell to 2, and the resulting mixture was stirred for three hours and then poured slowly into ten times the volume of distilled water. The white precipitate which separated out was collected by filtration, thoroughly washed with water until the washings were neutral, and dried, giving 13 g of modified polymer. IR spectral analysis showed the presence of amide II band near at 1550 cm$^{-1}$. It was also demonstrated that the peak near at 1780 cm$^{-1}$ derived from the acid anhydride ring had completely disappeared and a peak of carboxylic acid group had developed near at 1720 cm$^{-1}$. Calculation based on elemental analysis for C, H, N and O revealed that 23 mole % of the maleic anhydride units had reacted with p-aminosalicyclic acid to form amide bonding.

Lining Compositions

Two-pack lining compositions were prepared by combining an ethanolic solution of this modified polymer (10 weight %) with an ethanolic solution of tetrakis(acetylacetonato)zirconium (0.25 weight %) and with an ethanolic solution of dibutoxy bis-(acetylacetonato)zirconium (0.25 weight %), and their properties were evaluated in the same manner as Examples 1-3. The result is summarized in Table 5.

TABLE 5

| Lining Composition No. | Polymer | Zirconium Complex | Bonding Strength (Kg/cm$^2$) | Degree of Pentration | Marginal Leakage |
|---|---|---|---|---|---|
| I | Aminosalicylic acid-modified styrene/maleic acid copolymer | Tetrakis(acetylacetonato)zirconium | 9.2 | 0.1 | 0.1 |
| II | Aminosalicylic acid-modified styrene/maleic acid copolymer | Dibutoxy bis(acetylacetonato)zirconium | 8.3 | 0.2 | 0.1 |

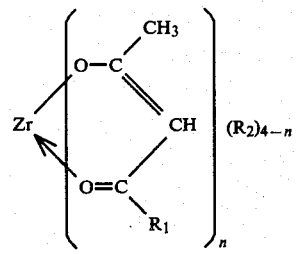

(wherein R$_1$ denotes —CH$_3$, —OCH$_3$ or —OCH$_2$CH$_3$, R$_2$ stands for an alkoxy of 2 to 10 carbon atoms, and n is an integer from 2 to 4).

2. The dental lining compositions as defined in claim 1, wherein said polymer is such that the quotient of the total number of carbon atoms in the molecule divided by the number of carboxyl groups contained is 4 or larger.

3. The dental lining compositions as defined in claim 2, wherein said polymer is a styrene/maleic acid copolymer.

4. The dental lining compositions as defined in claim 3, wherein said copolymer is a modified copolymer in which 10 to 60 mole % of the maleic acid units has been modified by aminosalicylic acid.

5. The dental lining compositions as defined in claim 1, wherein said zirconium chelate compound is tetrakis-(acetylacetonato)zirconium or dibutoxy bis-(acetylacetonato)zirconium.

What is claimed is:

1. Two-pack type dental lining compositions comprising (a) a solution of a polymer having at least 10 mole % of a carboxyl-containing vinyl monomer, and (b) a solution of a zirconium chelate compound represented by the following general formula

UNITED STATES PATENT AND TRADEMARK OFFICE
CERTIFICATE OF CORRECTION

PATENT NO. : 4,648,844
DATED : March 10, 1987
INVENTOR(S) : IKUO OMURA ET AL

It is certified that error appears in the above-identified patent and that said Letters Patent is hereby corrected as shown below:

In the Abstract, line 4, delete "monomer" and insert --monomeric unit--.

Column 2, line 24, delete "monomer" and insert --monomeric unit--;

lines 54-55, change "poly(fummaric acid)" to --poly(fumaric acid)--.

Column 6, line 29, change "spraing" to --spraying--.

Column 8, Table 1, under "Bond Strength", change "Kg" to --$kg/cm^2$--.

Claim 1, line 3, delete "monomer" and insert --monomeric unit--.

Signed and Sealed this

Third Day of November, 1987

Attest:

DONALD J. QUIGG

Attesting Officer

Commissioner of Patents and Trademarks